(12) United States Patent
Cunningham et al.

(10) Patent No.: US 7,452,838 B2
(45) Date of Patent: Nov. 18, 2008

(54) CONTROLLING TEMPERATURE IN CATALYST REGENERATORS

(75) Inventors: Brian A. Cunningham, Ellicott City, MD (US); Todd R. Steffens, Centreville, VA (US); James H. Beech, Jr., Kingwood, TX (US); Richard E. Walter, Long Valley, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 787 days.

(21) Appl. No.: 11/070,607

(22) Filed: Mar. 2, 2005

(65) Prior Publication Data

US 2006/0135348 A1 Jun. 22, 2006

Related U.S. Application Data

(60) Provisional application No. 60/638,766, filed on Dec. 22, 2004.

(51) Int. Cl.
*B01J 20/34* (2006.01)

(52) U.S. Cl. .............................. 502/41; 502/38; 502/45

(58) Field of Classification Search .................. 502/38, 502/41, 45
See application file for complete search history.

(56) References Cited

U.S. PATENT DOCUMENTS

| 2,487,961 | A | 11/1949 | Angell | 23/1 |
|---|---|---|---|---|
| 3,351,548 | A | 11/1967 | Payne et al. | 208/120 |
| 4,071,573 | A | 1/1978 | Owen et al. | 260/688 R |
| 4,167,492 | A | 9/1979 | Varady | 252/417 |
| 4,197,189 | A | 4/1980 | Thompson et al. | 208/164 |
| 4,340,566 | A | 7/1982 | Thompson et al. | 422/143 |
| 4,353,812 | A | 10/1982 | Lomas et al. | 252/417 |
| 4,374,750 | A | 2/1983 | Vickers et al. | 252/417 |
| 5,000,841 | A | 3/1991 | Owen | 208/113 |
| 5,158,919 | A | 10/1992 | Haddad et al. | 502/44 |
| 5,346,613 | A | 9/1994 | Lomas et al. | 208/164 |
| 5,455,010 | A | 10/1995 | Lomas et al. | 422/144 |
| 5,635,140 | A | 6/1997 | Miller et al. | 422/144 |
| 5,773,378 | A | 6/1998 | Bussey et al. | 502/41 |
| 5,800,697 | A | 9/1998 | Lengemann | 208/159 |
| 6,503,460 | B1 | 1/2003 | Miller et al. | 422/143 |
| 2003/0163010 | A1 | 8/2003 | Xu et al. | 585/638 |

*Primary Examiner*—Edward M Johnson

(57) ABSTRACT

This invention relates to efficiently regenerating catalyst particles by minimizing the formation of localized "hot spots" and "cold spots" in a regeneration zone. In one embodiment, the invention includes mixing spent catalyst from a reactor and cold catalyst from a catalyst cooler in a mixing zone and directing the mixed catalyst to the regeneration zone in a fluidized manner with a fluidizing medium. In the regeneration zone, the mixed catalyst contacts an oxygen-containing regeneration medium under conditions effective to regenerate the spent catalyst contained therein.

48 Claims, 2 Drawing Sheets

CONTROLLING TEMPERATURE IN CATALYST REGENERATORS

CROSS REFERENCE TO RELATED APPLICATIONS

Figure 1:
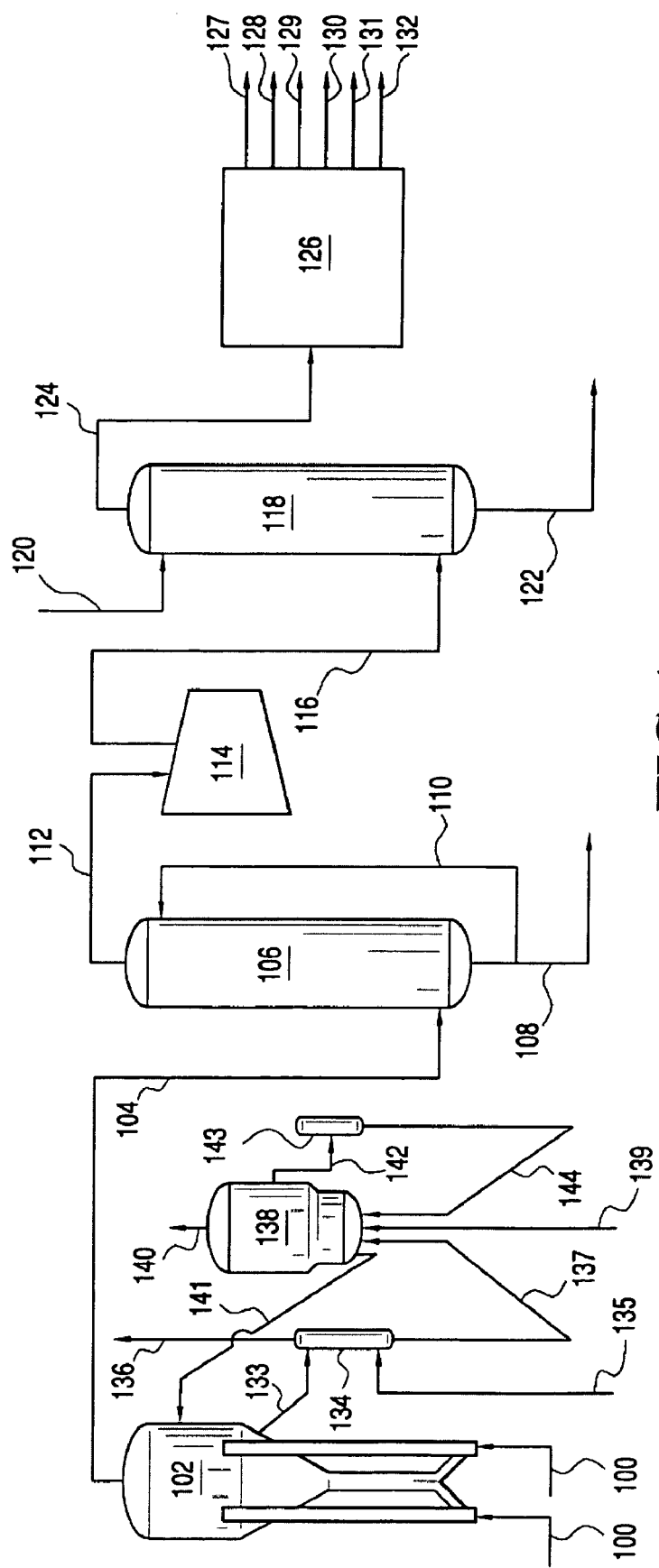

This application claims the benefit of Provisional Application No. 60/638,766 filed Dec. 22, 2004, the disclosure of which is fully incorporated herein by reference.

FIELD OF THE INVENTION

The present invention relates to regenerating catalyst. More particularly, the invention relates to controlling catalyst temperature during the regeneration process.

BACKGROUND OF THE INVENTION

Light olefins, defined herein as ethylene and propylene, serve as feeds for the production of numerous chemicals. Olefins traditionally are produced by petroleum cracking. Because of the limited supply and/or the high cost of petroleum sources, the cost of producing olefins from petroleum sources has increased steadily.

Alternative feedstocks for the production of light olefins are oxygenates, such as alcohols, particularly methanol, dimethyl ether, and ethanol. Alcohols may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for olefin production.

The catalysts used to promote the conversion of oxygenates to olefins are molecular sieve catalysts. Because ethylene and propylene are the most sought after products of such a reaction, research has focused on what catalysts are most selective to ethylene and/or propylene, and on methods for increasing the life and selectivity of the catalysts to ethylene and/or propylene.

The conversion of oxygenates to olefins (OTO), particularly the conversion of methanol to olefins (MTO), in a hydrocarbon conversion apparatus generates and deposits carbonaceous material (coke) on the molecular sieve catalysts used to catalyze the conversion process. Excessive accumulation of these carbonaceous deposits will interfere with the catalyst's ability to promote the reaction. In order to avoid unwanted build-up of coke on molecular sieve catalysts, the OTO and MTO processes incorporate a second step comprising catalyst regeneration. During regeneration, the coke is at least partially removed from the catalyst by combustion with oxygen, which restores the catalytic activity of the catalyst and forms a regenerated catalyst. The regenerated catalyst then may be reused to catalyze the conversion of methanol to olefins.

In conventional regeneration vessels, coked catalyst is directed from a reactor to a catalyst regenerator. In a catalyst regenerator, a regeneration medium, usually oxygen, enters the regenerator, and coke is removed from the coked catalyst by combustion with the regeneration medium to form regenerated catalyst and gaseous byproducts. The bulk of the regenerated catalyst from the regenerator is returned to the reactor. The gaseous byproducts are forced out an exhaust outlet oriented in the upper section of the catalyst regenerator.

The combustion of the carbonaceous deposits from molecular sieve catalyst compositions during catalyst regeneration is an exothermic process. The exothermic nature of catalyst regeneration presents a problem in OTO regeneration systems because the amount of coke formed on the molecular sieve catalyst compositions utilized in OTO reaction systems preferably is maintained at higher levels than in conventional FCC processes in order to maintain a high prime olefin (ethylene and propylene) selectivity. As a result, the amount of heat liberated from the OTO molecular sieve catalyst compositions during catalyst regeneration is significantly greater than the amount of heat liberated from the regeneration of catalysts in FCC processes.

The tremendous amount of heat liberated during the regeneration of heavily coked catalyst particles, such as coked OTO catalyst particles, may exceed the metal tolerances of the metals used to form the catalyst regenerator, particularly of the separation vessels, e.g., cyclone separators, contained therein as well as the conduits used to transport regenerated catalyst back to the hydrocarbon conversion apparatus. The creation of localized "hot spots" in catalyst regenerators also poses a significant problem in that catalyst is not regenerated uniformly throughout the regeneration zone. The heat also can damage the catalyst particles themselves. As a result, improved processes are sought for regenerating highly coked catalyst particles, such as coked catalyst particles derived from OTO reaction systems, while maintaining desirable temperature characteristics in the OTO catalyst regenerator.

SUMMARY OF THE INVENTION

The present invention provides processes and systems for regenerating catalyst, preferably heavily coked catalyst, in a regeneration system. The processes and systems provide the ability to regenerate the heavily coked catalyst while maintaining desirable temperature characteristics during the regeneration process. The processes and systems are ideally suited for implementation in an oxygenates to olefin (OTO) reaction system.

In one embodiment, the invention is to a process for regenerating catalyst, wherein the process comprises the steps of: (a) mixing spent catalyst from a reactor with cold catalyst from a catalyst cooler in a mixing zone to form a mixed catalyst; (b) contacting the mixed catalyst with a fluidizing medium under conditions effective to transport the mixed catalyst in a fluidized manner from the mixing zone to a regeneration zone; (c) contacting the mixed catalyst in the regeneration zone with an oxygen-containing regeneration medium under conditions effective to at least partially regenerate the mixed catalyst and form regenerated catalyst; (d) directing a first portion of the regenerated catalyst to the catalyst cooler, in which the first portion is cooled to form the cold catalyst mixed in step (a); and (e) directing a second portion of the regenerated catalyst to the reactor. In this process, the oxygen-containing regeneration medium optionally is added directly into the regeneration zone. In this embodiment, the ratio of the feed rate of regeneration medium fed to the regeneration zone to the feed rate of the fluidizing medium fed to the mixing zone optionally is greater than about 5, greater than about 50, or greater than about 98.

In another embodiment, the invention is to a process for regenerating catalyst, wherein the process comprises the steps of: (a) mixing spent catalyst from a reactor with cold catalyst from a catalyst cooler in a mixing zone to form a mixed catalyst; (b) directing a fluidizing medium into the mixing zone at a first feed rate under conditions effective to transport the mixed catalyst in a fluidized manner from the mixing zone to a regeneration zone; (c) directing an oxygen-containing regeneration medium into the regeneration zone at a second feed rate, wherein the second feed rate is greater than the first feed rate; (d) contacting the mixed catalyst in the regeneration zone with the oxygen-containing regeneration medium under conditions effective to at least partially regenerate the mixed catalyst and form regenerated catalyst; (e) directing a first portion of the regenerated catalyst to the catalyst cooler, in which the first portion is cooled to form the cold catalyst mixed in step (a); and (f) directing a second portion of the regenerated catalyst to the reactor. In this embodiment, the ratio of the second feed rate to the first feed rate is greater than about 5, greater than about 50 or greater than about 98.

Optionally, the fluidizing medium comprises an oxygen-containing fluidizing medium. In this embodiment, the fluidizing medium and the oxygen-containing regeneration medium optionally comprise the same oxygen-containing component. For example, the fluidizing medium and the oxygen-containing regeneration medium optionally comprise air.

Optionally, the process further comprises the step of: cooling the mixed catalyst in the mixing zone with a cooling medium, which cooling medium indirectly contacts the mixed catalyst in the mixing zone through one or more cooling coils. Optionally, the catalyst cooler comprises a plurality of external catalyst coolers operating in parallel.

Optionally, the transporting in step (b) comprises the substeps of: (i) directing the mixed catalyst in a fluidized manner upwardly through a vertically extending conduit; and (ii) distributing the mixed catalyst into the regeneration zone through one or more radially-extending downwardly-angled trough arms, a cap or a plate.

Optionally, the mixed catalyst is released into the regeneration zone substantially over one or more grids, which grids release the oxygen-containing regeneration medium into the regeneration zone.

Optionally, the spent catalyst comprises more than 0.5, more than 1, more than 2, more than 3, more than 4 or more than 5 weight percent coke, based on the total weight of the spent catalyst and coke thereon.

Optionally, the mixed catalyst in the mixing zone has a temperature of from about 427° C. to about 700° C., optionally from about 527° C. to about 600° C. The mixed catalyst and the regenerated catalyst in the regeneration zone optionally has a temperature of from about 527° C. to about 760° C., optionally from about 600° C. to about 732° C.

Optionally, the ratio of the flow rate of the first portion to the flow rate of the second portion is at least about 1.0, at least about 2.0 or at least about 4.0.

Optionally, the process further comprises the step of: directing a third portion of the regenerated catalyst from the regeneration zone directly to the mixing zone. The flow rate of the third portion optionally is adjustable with a valve to control the temperature of the mixed catalyst in the mixing zone.

In another embodiment, the invention is to a regeneration system, which comprises (a) a regeneration zone; (b) a catalyst cooler; (c) a mixing zone; (d) a spent catalyst conduit for communicating spent catalyst from a reactor to the mixing zone; (e) a hot catalyst conduit for communicating hot catalyst from the regeneration zone to the catalyst cooler; (f) a cold catalyst conduit for communicating cold catalyst from the catalyst cooler to the mixing zone; (g) a mixed catalyst conduit for communicating the mixed catalyst from the mixing zone to the regeneration zone; and (h) a regenerated catalyst conduit for communicating regenerated catalyst from the regeneration zone to the reactor.

Optionally, an oxygen-containing regeneration medium is added directly into the regeneration zone.

Optionally, the mixing zone is adapted to receive a fluidizing medium from a fluidizing medium source to transport catalyst in a fluidized manner from the mixing zone to the regeneration zone. The fluidizing medium optionally comprises an oxygen-containing fluidizing medium. The fluidizing medium and the oxygen-containing regeneration medium optionally comprise the same oxygen-containing component. For example, the fluidizing medium and the oxygen-containing regeneration medium optionally comprise air.

Optionally, the mixing zone comprises one or more coils for cooling the mixed catalyst contained therein. The catalyst cooler optionally comprises a plurality of external catalyst coolers operating in parallel.

Optionally, the mixed catalyst conduit comprises: a vertically extending conduit for transporting the mixed catalyst in an upward direction; and one or more radially-extending downwardly-angled trough arms for delivering the mixed catalyst to the regeneration zone. Optionally, the trough arms have one or more outlets that are situated substantially over one or more grids, which grids release the oxygen-containing regeneration medium into the regeneration zone.

Optionally, the system further comprises a temperature control catalyst conduit for communicating regenerated catalyst from the regeneration zone directly to the mixing zone. The temperature control catalyst conduit optionally comprises a valve for controlling the flow of the regenerated catalyst communicated so as to control the temperature of the mixed catalyst in the mixing zone. As a result, the valve also acts to control the temperature of the catalyst in the regeneration zone.

BRIEF DESCRIPTION OF THE FIGS.

Figure 2:
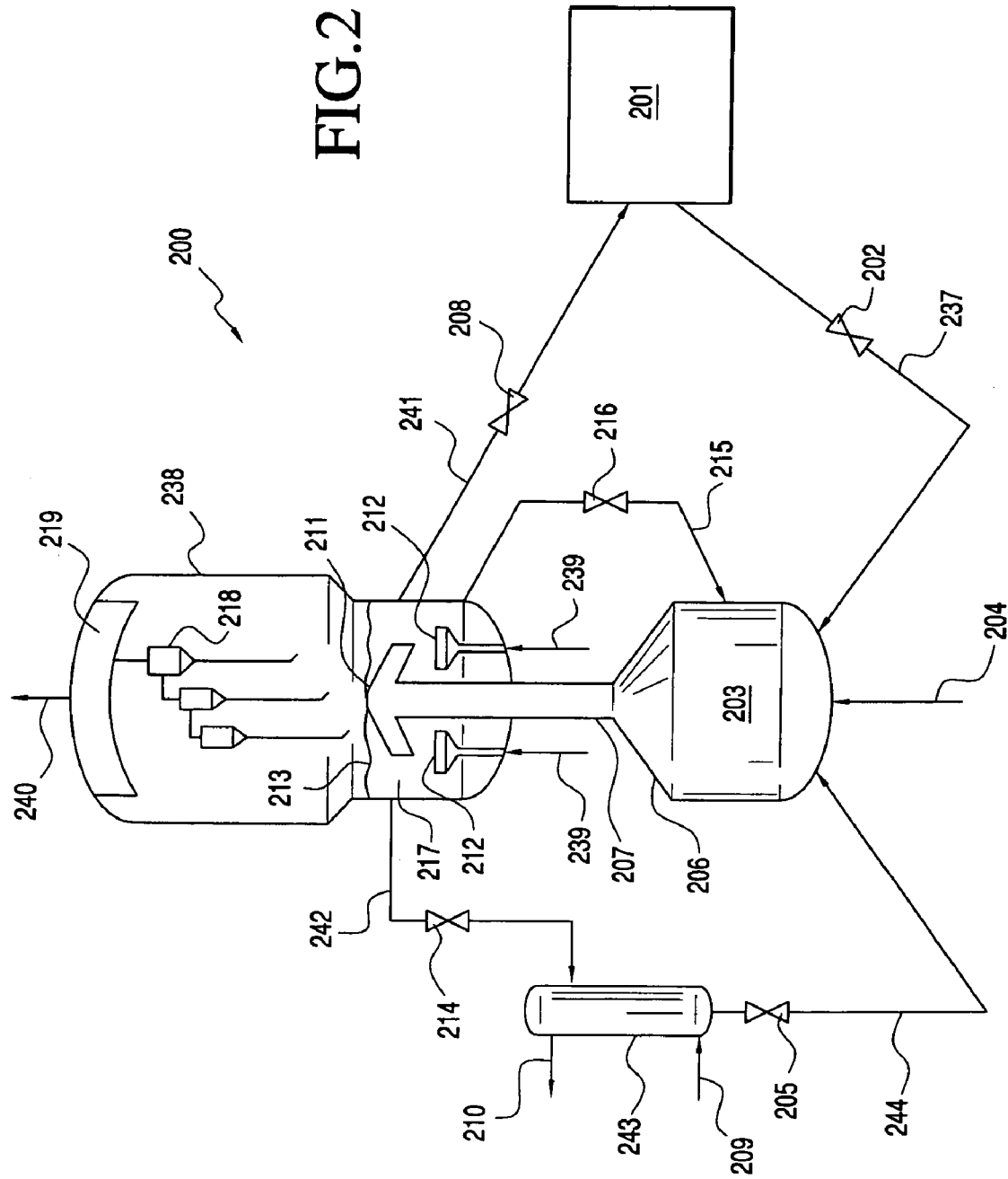

This invention will be better understood by reference to the Detailed Description of the Invention when taken together with the attached drawings, wherein:

FIG. 1 illustrates a flow diagram of an oxygenate to olefins reaction system having a catalyst regeneration system; and FIG. 2 illustrates a flow diagram of a catalyst regeneration system according to one embodiment of the present invention.

DETAILED DESCRIPTION OF THE INVENTION

I. Introduction

This invention relates to efficiently regenerating catalyst particles by minimizing the formation of localized "hot spots" in a regeneration zone. In one embodiment, the invention includes mixing spent catalyst from a reactor and cold catalyst from a catalyst cooler in a mixing zone and directing the mixed catalyst to the regeneration zone in a fluidized manner with a fluidizing medium. In the regeneration zone, the mixed catalyst contacts an oxygen-containing regeneration medium under conditions effective to regenerate the spent catalyst contained therein.

II. Oxygenate to Olefin Reaction Systems

As indicated above, the present invention is directed to controlling the temperature of catalyst regeneration, preferably in an OTO reaction process. OTO reaction systems will now be described in greater detail. As used herein, "reaction system" means a system comprising a reactor, a catalyst cooler, optionally a catalyst regenerator, and optionally a catalyst stripper. The reactor comprises a reaction unit, which defines a reaction zone, and optionally a disengaging unit, which defines a disengaging zone.

In an OTO reaction system, a molecular sieve catalyst composition is used to convert an oxygenate-containing feedstock to light olefins. Ideally, the molecular sieve catalyst composition comprises an alumina or a silica-alumina catalyst composition. Silicoaluminophosphate (SAPO) molecular sieve catalysts are particularly desirable in such conversion processes, because they are highly selective in the formation of ethylene and propylene. A non-limiting list of preferable SAPO molecular sieve catalyst compositions includes SAPO-17, SAPO-18, SAPO-34, SAPO-35, SAPO-44, the substituted forms thereof, and mixtures thereof. The molecular sieve catalyst composition fluidized according to the present invention optionally comprises a molecular sieve selected from the group consisting of: SAPO-5, SAPO-8, SAPO-1, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof. Additionally or alternatively, the molecular sieve comprises an aluminophosphate (ALPO) molecular sieve. Preferred ALPO molecular sieves include ALPO-5, ALPO-11, ALPO-18, ALPO-31, ALPO-34, ALPO-36, ALPO-37, ALPO-46, AEI/CHA intergrowths, mixtures thereof, and metal containing forms thereof. Ideally, the catalyst to regenerated according to the present invention comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, a zeolitic molecular sieve, ZSM-34, ZSM-5, metal containing forms thereof, intergrown forms thereof, AEI/CHA intergrowths, and mixtures thereof.

The oxygenate-containing feedstock that is directed to an OTO reaction system optionally contains one or more aliphatic-containing compounds such as alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and more preferably from 1 to 4 carbon atoms, and most preferably methanol.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as DME, diethyl ether and methylethyl ether, alkyl-halides such as methyl chloride and ethyl chloride, alkyl ketones such as dimethyl ketone, alkyl-aldehydes such as formaldehyde and acetaldehyde, and various acids such as acetic acid.

In a preferred embodiment of the process of the invention, the feedstock contains one or more organic compounds containing at least one oxygen atom. In the most preferred embodiment of the process of invention, the oxygenate in the feedstock comprises one or more alcohols, preferably aliphatic alcohols where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, DME, diethyl ether, di-isopropyl ether, formaldehyde, dimethyl carbonate, dimethyl ketone, acetic acid, and mixtures thereof. In the most preferred embodiment, the feedstock comprises one or more of methanol, ethanol, DME, diethyl ether or a combination thereof.

The various feedstocks discussed above are converted primarily into one or more olefins. The olefins or olefin monomers produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomers include unsaturated monomers, diolefins having 4 to 18 carbon atoms, conjugated or nonconjugated dienes, polyenes, vinyl monomers and cyclic olefins.

In a preferred embodiment, the feedstock, which ideally comprises methanol, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as an oxygenate-to-olefins (OTO) reaction process. In an OTO process, typically an oxygenated feedstock, most preferably a methanol- and ethanol-containing feedstock, is converted in the presence of a molecular sieve catalyst composition into one or more olefins, preferably and predominantly, ethylene and/or propylene, referred to herein as light olefins.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677, 242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor type are riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The conversion temperature employed in the conversion process, specifically within the reactor system, is in the range of from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.) most preferably from about 662° F. (350° C.) to about 1022° F. (550° C.).

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $h^-$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol, DME, or both, is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

FIG. 1 illustrates a non-limiting exemplary OTO reaction system. In the figure, an oxygenate-containing feedstock is directed through lines 100 to an OTO fluidized reactor 102 wherein the oxygenate (preferably comprising methanol) in the oxygenate-containing feedstock contacts a molecular sieve catalyst composition under conditions effective to convert the oxygenate to light olefins and various byproducts, which are yielded from the fluidized reactor 102 in an olefin-containing stream in line 104. The olefin-containing stream in line 104 optionally comprises methane, ethylene, ethane, propylene, propane, various oxygenate byproducts, C4+ olefins, water and hydrocarbon components. The olefin-containing stream in line 104 is directed to a quench unit or quench tower 106 wherein the olefin-containing stream in line 104 is cooled and water and other readily condensable components are condensed.

The condensed components, which comprise water, are withdrawn from the quench tower 106 through a bottoms line 108. A portion of the condensed components are recycled through line 110 back to the top of the quench tower 106. The components in line 110 preferably are cooled in a cooling unit, e.g., heat exchanger (not shown), so as to provide a cooling medium to cool the components in quench tower 106.

An olefin-containing vapor is yielded from the quench tower 106 through overhead stream 112. The olefin-containing vapor is compressed in one or more compressors 114 and the resulting compressed olefin-containing stream is optionally passed through line 116 to a water absorption unit 118. Methanol is preferably used as the water absorbent, and is fed to the top portion of the water absorption unit 118 through line 120. Methanol and entrained water, as well as some oxygenates, are separated as a bottoms stream through line 122. The light olefins are recovered through an overhead effluent stream 124, which comprises light olefins. Optionally, the effluent stream 124 is sent to an additional compressor or compressors, not shown, and a heat exchanger, not shown. Ultimately, the effluent stream 124 is directed to separation system 126, which optionally comprises one or more separation units such as $CO_2$ removal unit(s) (e.g., caustic tower(s)), distillation columns, absorption units, and/or adsorption units.

The separation system 126 separates the components contained in the overhead line 124. Thus, separation system 126 forms a light ends stream 127, optionally comprising methane, hydrogen and/or carbon monoxide; an ethylene-containing stream 128 comprising mostly ethylene; an ethane-containing stream 129 comprising mostly ethane; a propylene-containing stream 130 comprising mostly propylene; a propane-containing stream 131 comprising mostly propane; and one or more byproduct streams, shown as line 132, comprising one or more of the oxygenate byproducts, provided above, heavy olefins, heavy paraffins, and/or absorption mediums utilized in the separation process. Separation processes that may be utilized to form these streams are well-known and are described, for example, in pending U.S. patent applications Ser. Nos. 10/124,859 filed Apr. 18, 2002; Ser. No. 10/125,138 filed Apr. 18, 2002; Ser. No. 10/383,204 filed Mar. 6, 2003; and Ser. No. 10/635,410 filed Aug. 6, 2003, the entireties of which are incorporated herein by reference.

FIG. 1 also illustrates a conventional catalyst regeneration system, which is in fluid communication with fluidized reactor 102. As shown, at least a portion of the catalyst compositions contained in fluidized reactor 102 are withdrawn and transported, preferably in a fluidized manner, in conduit 133 from the fluidized reactor 102 to a catalyst stripper 134. In the catalyst stripper 134, the catalyst compositions contact a stripping medium, e.g., steam and/or nitrogen, under conditions effective to remove interstitial hydrocarbons from the molecular sieve catalyst compositions. As shown, stripping medium is introduced into catalyst stripper 134 through line 135, and the resulting stripped stream 136 is released from catalyst stripper 134. Optionally, all or a portion of stripped stream 136 is directed back to fluidized reactor 102.

During contacting of the oxygenate feedstock with the molecular sieve catalyst composition in the fluidized reactor 102, the molecular sieve catalyst composition may become at least partially deactivated. That is, the molecular sieve catalyst composition becomes at least partially coked. In order to reactivate the molecular sieve catalyst composition, the catalyst composition preferably is directed to a catalyst regenerator 138. As shown, the stripped catalyst composition is transported, preferably in the fluidized manner, from catalyst stripper 134 to catalyst regenerator 138 in conduit 137. Preferably, the stripped catalyst composition is transported in a fluidized manner through conduit 137.

In catalyst regenerator 138, the stripped catalyst composition contacts a regeneration medium, preferably comprising oxygen, under conditions effective (preferably including heating the coked catalyst) to at least partially regenerate the catalyst composition contained therein. As shown, the regeneration medium is introduced into the catalyst regenerator 138 through line 139, and the resulting regenerated catalyst compositions are ultimately transported, preferably in a fluidized manner, from catalyst regenerator 138 back to the fluidized reactor 102 through conduit 141. The gaseous combustion products are released from the catalyst regenerator 138 through flue gas stream 140. In another embodiment, not shown, the regenerated catalyst composition additionally or alternatively is directed, optionally in a fluidized manner, from the catalyst regenerator 138 to one or more of the fluidized reactor 102 and/or the catalyst stripper 134. In one embodiment, not shown, a portion of the catalyst composition in the reaction system is transported directly, e.g., without first passing through the catalyst stripper 134, optionally in a fluidized manner, from the fluidized reactor 102 to the catalyst regenerator 138.

As the catalyst compositions contact the regeneration medium in catalyst regenerator 138, the temperature of the catalyst composition will increase due to the exothermic nature of the regeneration process. As a result, it is desirable to control the temperature of the catalyst composition by directing at least a portion of the catalyst composition from the catalyst regenerator 138 to a catalyst cooler 143. As shown, the catalyst composition is transported in a fluidized manner from catalyst regenerator 138 to the catalyst cooler 143 through conduit 142. The resulting cold catalyst composition is transported, preferably in a fluidized manner from catalyst cooler 143 back to the catalyst regenerator 138 through conduit 144. In another embodiment, not shown, the cold catalyst composition additionally or alternatively is directed, optionally in a fluidized manner, from the catalyst cooler 143 to one or more of the fluidized reactor 102 and/or the catalyst stripper 134.

The processes and systems for controlling temperature in a catalyst regenerator according to the present invention will now be described in greater detail.

III. Process for Controlling the Temperature During Catalyst Regeneration

The regeneration systems and processes of the present invention allow for regenerating heavily coked catalyst particles while controlling the temperature of the regeneration process, e.g., maintaining temperatures below the metallurgical limitations of the metal(s) used to form the various components in the regeneration systems. The catalyst regeneration systems and processes of the present invention are particularly well-suited for the regeneration of heavily coked catalyst particles that are derived from OTO reaction systems. For purposes of the present specification and appended claims, the terms "coked catalyst" and "spent catalyst" are used interchangeably to refer to a catalyst composition that has been at least partially coked.

During the catalytic conversion of hydrocarbons to various products, e.g., the catalytic conversion of oxygenates to light olefins (the OTO process), carbonaceous deposits accumulate on the catalyst used to promote the conversion reaction. At some point, the build up of these carbonaceous deposits causes a reduction in the capability of the catalyst to function efficiently. For example, in the OTO process, an excessively "coked" catalyst does not readily convert the oxygenate feed to light olefins. At this point, the catalyst is partially deactivated. When a catalyst can no longer convert the hydrocarbon to the desired product, the catalyst is considered to be fully deactivated. The catalyst regenerator of the present invention efficiently removes at least a portion of the carbonaceous deposits from an at least partially coked catalyst composition to form a regenerated catalyst composition having increased catalytic activity over the at least partially coked catalyst composition.

In accordance with the present invention, as discussed in more detail below, spent catalyst is withdrawn from a hydrocarbon conversion apparatus (HCA), e.g., a reactor or reaction unit, and is directed to a mixing zone, where the spent catalyst is mixed with cold catalyst to form mixed catalyst. The mixed catalyst is then directed to the catalyst regenerator. Preferably, the HCA comprises an OTO reactor, and most preferably a methanol to olefin (MTO) reactor. The mixed catalyst (which comprises the spent catalyst) is partially, if not fully, regenerated in the catalyst regenerator to form regenerated catalyst. By regeneration, it is meant that the carbonaceous deposits are at least partially removed from the catalyst. Desirably, the catalyst withdrawn from the HCA is at least partially coked and, thus, at least partially deactivated or spent. The remaining portion of catalyst in the HCA is recirculated in the HCA without being directed to the regeneration system. The regenerated catalyst, with or without cooling, is then returned to the HCA.

Desirably, a portion of the catalyst, comprising molecular sieve and any other materials such as matrix materials, binders, fillers, etc., is removed from the HCA for regeneration and recirculation back to the HCA at a rate (catalyst weight/hour) of from about 0.05 times to about 1 times, more desirably from about 0.1 times to about 0.5 times, and most desirably from about 0.1 to about 0.3 times the total feed rate (oxygenate weight/hour) of oxygenates to the HCA. These rates pertain to the formulated molecular sieve catalyst composition, including non-reactive solids.

The catalyst can be regenerated in any number of methods, such as batch, continuous, semi-continuous, or a combination thereof. Continuous catalyst regeneration is a desired method. Desirably, the catalyst is regenerated to a level of remaining coke from about 0.01 weight percent to about 15 weight percent, more preferably from about 0.01 to about 5 weight percent, based on the total weight of the regenerated catalyst composition.

A majority of the catalyst regeneration occurs in a regeneration zone, the temperature of which preferably is maintained from about 527° C. to about 760° C., and optionally from about 600° C. to about 732° C. Because the regeneration reaction preferably takes place at a temperature considerably higher than the OTO conversion reaction, e.g., about 93° C. to about 150° C. higher, it is desirable to cool at least a portion of the regenerated catalyst to a lower temperature before it is sent back to the HCA. One or more catalyst coolers, preferably located externally to the catalyst regenerator, are used to remove heat from the regenerated catalyst after it has been withdrawn from the catalyst regenerator.

The particular type of catalyst cooler implemented in the present invention may vary widely. Preferably, the catalyst cooler comprises a shell and tube type heat exchanging device or a jacketed pipe heat exchange device. Included in the category of shell and tube type heat exchange devices are bayonet tube (tube-inside-tube) exchangers and U-tube exchangers.

When the regenerated catalyst is cooled, it is optionally cooled to a temperature that is from about 70° C. higher to about 80° C. cooler than the temperature of the catalyst withdrawn from the HCA. As discussed in greater detail below, this cold catalyst is then directed, at least in part, to the mixing zone, where it is admixed with the spent catalyst from the HCA. A portion of the regenerated catalyst from the catalyst regenerator is returned to the HCA. The returned portion can be returned to any portion of the HCA. For example, the regenerated catalyst can be returned to a catalyst containment area to await contact with the feed, a separation zone to contact products of the feed or a combination of both.

Ideally, regeneration occurs in the catalyst regenerator at a pressure of from about 5 psig (34.5 kPag) to about 50 psig (345 kPag), preferably from about 15 psig (103 kPag) to about 40 psig (276 kPag), and most preferably from about 20 psig (138 kPag) to about 30 psig (207 kPag). The precise regeneration pressure is dictated by the pressure in the HCA. Higher pressures are generally preferred for lowering equipment size and catalyst inventory, however, higher pressures increase air blower power and cost.

Desirably, catalyst regeneration is carried out after the at least partially deactivated catalyst has been stripped of most of the readily removable organic materials (organics), e.g., interstitial hydrocarbons, in a stripper or stripping chamber. This stripping can be achieved by passing a stripping medium, e.g., a stripping gas, over the spent catalyst at an elevated temperature. Gases suitable for stripping include steam, nitrogen, helium, argon, methane, $CO_2$, CO, hydrogen, and mixtures thereof. A preferred gas is steam. The gas hourly space velocity (GHSV) of the stripping gas, based on volume of gas to volume of catalyst and coke, is from about 0.1 $hr^{-1}$ to about 20,000 $hr^{-1}$. Acceptable temperatures of stripping are from about 250° C. to about 750° C., and desirably from about 400° C. to about 600° C. Acceptable stripping pressures are from about 5 psig (34.5 kPag) to about 50 psig (344 kPag), more preferably from about 10 psig (69.0 kPag) to about 30 psig (207 kPag), and most preferably from about 20 psig (138 kPag) to about 25 psig (172 kPag). The stripping pressure is largely dependent upon the pressure in the HCA and in the catalyst regenerator.

The catalyst regenerator of the present invention includes a regeneration zone and a separation zone. In the regeneration zone, the at least partially coked catalyst (spent catalyst) contacts the regeneration medium, preferably as a turbulent dense bed or phase, under conditions effective, e.g., temperature and pressure, to at least partially regenerate the at least partially coked catalyst. Specifically, the conditions preferably are effective to convert the at least partially coked catalyst and the regeneration medium to regenerated catalyst and gaseous byproducts of the regeneration process. The regenerated catalyst may be fully or partially regenerated. The gaseous byproducts, optionally with entrained catalyst and/or unreacted regeneration medium, exit the dense phase and form a dilute phase, which extends from the surface of the dense phase to the top of the separation zone. The separation zone is adapted to separate the entrained catalyst from the gaseous components in the dilute phase, and return the entrained catalyst to the regeneration zone.

The dense phase density will depend on the solids particle density and the superficial gas velocity. Preferably, the density of the dense phase will range from about 10 $lb/ft^3$ (160.2 $kg/m^3$) to about 50 $lb/ft^3$ (800.9 $kg/m^3$), preferably from about 15 $lb/ft^3$ (240.3 $kg/m^3$) to about 35 $lb/ft^3$ (560.6 $kg/m^3$) and most preferably from about 20 $lb/ft^3$ (320.4 $kg/m^3$) to about 30 $lb/ft^3$ (480.6 $kg/m^3$). The superficial velocity in the dense phase optionally is no greater than 5 ft/sec (1.5 m/s), no greater than 4 ft/sec (1.22 m/s), no greater than 2 ft/sec (0.61 m/s), no greater than 1 ft/sec (0.30 m/s) or no greater than 0.5 ft/sec (0.15 m/s). Velocities much higher than 4 ft/sec (1.22 m/s) will result in a transition from a turbulent dense bed to a circulating fast fluid bed. In terms of lower range limits, the superficial velocity of the dense phase optionally is at least 0.1 ft/sec (0.03 m/s), at least 0.25 ft/sec (0.08 m/s), at least 0.5 ft/sec (0.15 m/s), or at least 0.75 ft/sec (0.23 m/s). Preferably, however, the superficial velocity in the dense phase ranges from 1.5 ft/sec (0.46 m/s) to 4.5 ft/sec (1.37 m/s), from 2.0 ft/sec (0.61 m/s) to 4.0 ft/sec (1.22 m/s), or from 2.5 ft/sec (0.76 m/s) to 3.5 ft/sec (1.07 m/s).

The mixing zone includes one or more catalyst inlets for receiving an at least partially coked catalyst from a hydrocarbon conversion apparatus (HCA), typically a reactor or reaction unit. In one embodiment, the at least partially coked catalyst is transported in a catalyst supply conduit, e.g., a tubular member, from the HCA or an intermediate vessel, e.g., a catalyst stripper, to the mixing zone for admixture with cold catalyst. A catalyst transport conduit (also referred to herein as a mixed catalyst conduit) then directs the mixed catalyst to the catalyst regenerator, as discussed in more detail below with reference to the figures. In the transport conduit (as well as preferably in the mixing zone), the mixed catalyst preferably comes in contact with a fluidization medium under conditions effective to fluidize the catalyst contained therein.

The transport conduit preferably enters the regeneration zone of the catalyst regenerator and releases the mixed catalyst (including spent catalyst) into the regeneration zone for carbonaceous deposit removal. The transport conduit optionally includes a plurality of second ends for evenly distributing the at least partially coked catalyst in the regeneration zone. In one preferred embodiment, the second end extends into the regeneration zone, preferably longitudinally with respect to the catalyst regenerator, and passes through a laterally extending distributor grid, through which the regeneration medium is introduced into the regeneration zone. In this embodiment, the second end releases the at least partially coked catalyst composition into the regeneration zone at a position above the distributor grid. The bulk of the regeneration process preferably occurs in the dense phase of the regeneration zone. The dense phase optionally comprises from about 2 to about 45 volume percent, preferably from about 20 to about 35 percent of the regeneration zone, based on the total volume of the regeneration zone. On a weight basis, the dense phase preferably comprises from about 45 to about 98 percent, optionally from about 85 to about 95 percent, of the catalyst in the regeneration zone.

As used herein, longitudinal means extending in a direction perpendicular to grade, e.g., vertical, and lateral means extending in a direction parallel to grade, e.g., horizontal. The proximal end of an object is the portion of the object that is nearest to grade, and the distal end of the object is the portion of the object that is furthest removed from grade.

The regeneration zone also preferably includes one or more regeneration medium inlets for receiving a regeneration medium, preferably air, molecular oxygen, or a mixture thereof. One or more regeneration medium conduits carry the regeneration medium from a regeneration medium source, such as a pressurized regeneration medium containment vessel in which the regeneration medium is stored, to the one or more regeneration medium inlets. In one embodiment, one or more nozzles introduce the regeneration medium into the regeneration zone. Preferably, the regeneration medium is introduced into the catalyst regenerator at a rate of about 50 to about 500 standard cubic feet (scf)/lb coke burned (about 3.1 to about 31.2 standard cubic meters (scm)/kg coke burned), more preferably from about 150 to about 400 scf/lb coke burned (about 9.4 to about 25.0 scm/kg coke burned), and most preferably from about 200 to about 350 scf/lb coke burned (about 12.5 to about 21.9 scm/kg coke burned).

As indicated above, the present invention specifically provides processes and systems for regenerating catalyst, preferably heavily coked catalyst, in a regeneration system. The processes and systems provide the ability to regenerate the heavily coked catalyst while minimizing the formation of "hot-spots" in the regeneration zone (including in one or more separation devices contained therein) or in any of the conduits associated with the regeneration zone. For purposes of the present specification and claims, the term "hot spot" means any region where the local temperature is hot enough to damage either the catalyst, keeping in mind the residence time of the catalyst in the hot region, or to damage any internal mechanical equipment which is designed based on some average or normal range of regenerator temperatures. The processes and systems are ideally suited for implementation in an oxygenates to olefin (OTO) reaction system, discussed above.

In one embodiment, the invention is to a process for regenerating catalyst, wherein the process comprises the steps of: (a) mixing spent catalyst from a reactor with cold catalyst from a catalyst cooler in a mixing zone to form a mixed catalyst; (b) contacting the mixed catalyst with a fluidizing medium under conditions effective to transport the mixed catalyst in a fluidized manner from the mixing zone to a regeneration zone; (c) contacting the mixed catalyst in the regeneration zone with an oxygen-containing regeneration medium under conditions effective to at least partially regenerate the mixed catalyst and form regenerated catalyst; (d) directing a first portion of the regenerated catalyst to the catalyst cooler, in which the first portion is cooled to form the cold catalyst mixed in step (a); and (e) directing a second portion of the regenerated catalyst to the reactor.

Preferably, the mixed catalyst is communicated to the regeneration zone from the mixing zone through a transport conduit, e.g., a pipe or tubing, also referred to herein as a "mixed catalyst conduit." Thus, the contacting of the mixed catalyst with the fluidizing medium (step (b)) transports the mixed catalyst in a fluidized manner from the mixing zone to the regeneration zone through the transport conduit. The lateral cross-sectional area of the transport conduit may vary widely, but preferably is less than the lateral cross-sectional area of the regeneration zone, although it could also be greater. Optionally, the lateral cross-sectional area of the transport conduit is less than the lateral cross-sectional area of the mixing zone, although it may also be greater. Optionally, the ratio of the lateral cross sectional area of the mixing zone to the lateral cross-sectional area of the transport conduit ranges from about from about 0.25 to about 2.0, more preferably from about 0.5 to about 1.5. In one embodiment, the ratio of the lateral cross sectional area of the mixing zone to the lateral cross-sectional area of the transport conduit is about 1. In this embodiment, the mixing zone may be a section of the transport conduit, and the boundary between the mixing zone and the transport conduit may be not be precisely defined.

The composition of the fluidizing medium may vary widely, but preferably the fluidizing medium comprises an oxygen-containing fluidizing medium. The oxygen-containing fluidizing medium comprises molecular oxygen or other oxidants. Optionally, the oxygen-containing fluidizing medium comprises an oxidant selected from the group consisting of: singlet $O_2$, $O_3$, $SO_3$, $N_2O$, NO, $NO_2$, $N_2O_5$, and mixtures thereof. Air and air diluted with nitrogen or $CO_2$ are particularly desirable fluidizing mediums. The oxygen concentration in air can be reduced to a controlled level to minimize overheating of, or creating hot spots in, the mixing zone, the catalyst transport conduit, and/or the catalyst regenerator. Additionally or alternatively, the fluidizing medium comprises hydrogen, mixtures of hydrogen and carbon monoxide, or other suitable reducing gases. In another embodiment, the fluidizing medium comprises steam, natural gas, nitrogen, argon, carbon dioxide, other inert gases, or mixtures thereof. Due to combustion and heat release concerns, hydrogen and natural gas fluidizing mediums are not preferred for lift lines that direct catalyst to a catalyst regenerator.

Desirably, the regeneration medium, preferably a gas, comprises molecular oxygen or other oxidants. Examples of other oxidants include, but are not necessarily limited to, singlet $O_2$, $O_3$, $SO_3$, $N_2O$, NO, $NO_2$, $N_2O_5$, and mixtures thereof. Air and air diluted with nitrogen or $CO_2$ are particularly desirable regeneration mediums. The oxygen concentration in air can be reduced to a controlled level to minimize overheating of, or creating hot spots in, the catalyst regenerator. The catalyst can also be regenerated reductively with hydrogen, mixtures of hydrogen and carbon monoxide, or other suitable reducing gases.

As indicated above, the fluidizing medium optionally comprises an oxygen-containing fluidizing medium. In this embodiment, the fluidizing medium and the oxygen-containing regeneration medium optionally comprise the same oxygen-containing component. For example, the fluidizing medium and the oxygen-containing regeneration medium optionally comprise air. Alternatively, the fluidizing medium and the oxygen-containing regeneration medium comprise different oxygen-containing components. In this embodiment, the fluidizing medium preferably comprises a first oxygen-containing component, which preferably comprises molecular oxygen or other oxidant. Examples of other oxidants include, but are not necessarily limited to, singlet $O_2$, $O_3$, $SO_3$, $N_2O$, NO, $NO_2$, $N_2O_5$, and mixtures thereof. Air and air diluted with nitrogen or $CO_2$ are particularly desirable fluidizing mediums. The oxygen concentration in air can be reduced to a controlled level to minimize overheating of, or creating hot spots in, the transport conduit and/or the catalyst regenerator. In this embodiment, the oxygen-containing regeneration medium preferably comprises a second oxygen-containing component, which is different from the first oxygen-containing component.

Preferably, the oxygen-containing regeneration medium is added directly into the regeneration zone rather than to the mixing zone or to the transport conduit that communicates the mixed catalyst from the mixing zone to the regeneration zone. In this embodiment, the ratio of the feed rate (by weight) of the regeneration medium fed to the regeneration zone to the feed rate of the fluidizing medium fed to the mixing zone preferably is greater than about 5, more preferably greater than about 50, and most preferably greater than about 98. The most desirable ratio will be a function of the actual coke concentration on the spent catalyst received in the mixing zone and would be optimized to yield the desired mix zone temperature.

Accordingly, in one embodiment, the invention is to a process for regenerating catalyst, wherein the process comprises the steps of: (a) mixing spent catalyst from a reactor with cold catalyst from a catalyst cooler in a mixing zone to form a mixed catalyst; (b) directing a fluidizing medium into the mixing zone at a first feed rate under conditions effective to transport the mixed catalyst in a fluidized manner from the mixing zone to a regeneration zone; (c) directing an oxygen-containing regeneration medium into the regeneration zone at a second feed rate, wherein the second feed rate is greater than the first feed rate; (d) contacting the mixed catalyst in the regeneration zone with the oxygen-containing regeneration medium under conditions effective to at least partially regenerate the mixed catalyst and form regenerated catalyst; (e) directing a first portion of the regenerated catalyst to the catalyst cooler, in which the first portion is cooled to form the cold catalyst mixed in step (a); and (f) directing a second portion of the regenerated catalyst to the reactor. In this embodiment, the ratio of the second feed rate (by weight) to the first feed rate (by weight) is greater than about 5, greater than about 50 or greater than about 98. In this embodiment, the ratio of the flow rate (by weight) of the first portion to the flow rate (by weight) of the second portion optionally is at least about 1.0, at least about 2.0 or at least about 4.0.

Thus, in a preferred embodiment, the fluidizing medium comprises an oxygen-containing fluidizing medium, and the volumetric flow rate of the regeneration medium fed to the regeneration zone is greater, ideally significantly greater, than the flow rate of the fluidizing medium fed to the mixing zone (and ultimately to the regeneration zone). By providing significantly more regeneration medium directly to the regeneration zone than the amount of oxygen-containing fluidizing medium that is directed to the mixing zone, the formation of hot spots in the mixing zone and the transport conduit can be advantageously minimized.

The ratio of the feed rate (by weight) of the cold catalyst fed to the mixing zone to the feed rate of the spent catalyst fed to the mixing zone may vary widely depending, among other things, on the particular fluidizing medium used, the amount of coke on the spent catalyst and the desired temperature of the catalyst in the mixing zone and/or in the regeneration zone. Ideally, the feed rate (by weight) of cold catalyst fed to the mixing zone relative to the feed rate (by weight) of spent catalyst fed to the mixing zone is monitored to maintain the average temperature of the mixed catalyst in the mixing zone at a temperature below material (e.g., metallurgical) constraints of the material(s) used to form the mixing zone and/or the transport conduit, e.g., less than about 980° C. (1800° F.), more preferably less than about 815° C. (1500° F.), and most preferably less than about 760° C. (1400° F.). Of course, the material constraints will depend on the thermodynamic characteristics of the material(s) used to form the mixing zone and the transport conduit. Optionally, the mixed catalyst in the mixing zone has a temperature of from about 427° C. to about 700° C., optionally from about 527° C. to about 600° C.

Additionally or alternatively, the feed rate (by weight) of the cold catalyst to the mixing zone relative to the feed rate (by weight) of the spent catalyst fed to the mixing zone is monitored to maintain the average temperature of the catalyst in the regeneration zone at a temperature below metallurgical constraints, e.g., less than about 980° C. (1800° F.), more preferably less than about 815° C. (1500° F.), and most preferably less than about 760° C. (1400° F.). In one embodiment, the feed rate (by weight) of cold catalyst fed to the mixing zone relative to the feed rate (by weight) of spent catalyst fed to the mixing zone is monitored to maintain the average temperature of the catalyst in the regeneration zone at a temperature less than about 980° C. (1800° F.), more preferably less than about 815° C. (1500° F.), and most preferably less than about 760° C. (1400° F.). Optionally, the mixed catalyst and the regenerated catalyst in the regeneration zone has a temperature of from about 527° C. to about 760° C., optionally from about 600° C. to about 732° C.

The ratio of the flow rate (by weight) of the first portion of the regenerated catalyst to the flow rate (by weight) of the second portion of the regenerated catalyst may vary widely depending, among other things, on the particular fluidizing medium used, the amount of coke on the spent catalyst, the regeneration conditions implemented in the regeneration zone, etc. Optionally, the flow rate (by weight) of the first portion to the flow rate (by weight) of the second portion is at least about 1.0, at least about 2.0 or at least about 4.0.

In one embodiment, the process further comprises the step of: cooling the mixed catalyst in the mixing zone with a cooling medium. The cooling medium preferably indirectly contacts the mixed catalyst in the mixing zone through one or more cooling coils. This aspect of the present invention advantageously provides the ability to maintain an even temperature distribution within the mixing zone. Additionally, this aspect of the invention provides the ability to directly control temperature without changing catalyst flow rates.

Optionally, the mixed catalyst is released into the regeneration zone substantially over one or more grids in the regeneration zone. The grids release the oxygen-containing regeneration medium into the regeneration zone. This aspect of the invention provides for uniform contacting of the mixed catalyst with the regeneration medium in the regeneration zone. U.S. Pat. Nos. 5,635,140 and 6,503,460, the entireties of which are incorporated herein by reference, fully describe regeneration systems in which a regeneration medium is introduced through a plurality of grids into a catalyst regenerator, and in which spent catalyst is introduced into the catalyst regenerator over the grids.

As indicated above, the present invention is ideally suited for regenerating highly coked catalyst while minimizing the formation of hot spots in the regeneration system. It has been discovered that spent catalyst derived from an OTO reaction system has a significantly higher coke on catalyst level than spent catalyst derived from fluidized catalytic cracking reaction systems. For example, the spent catalyst derived from an OTO reaction system may comprise more than 0.5, more than 1, more than 2, more than 3, more than 4 or more than 5 weight percent coke, based on the total weight of the spent catalyst and coke thereon. Such highly coked catalyst particles may be easily regenerated in according to the processes and systems of the present invention.

Optionally, the process further comprises the step of: directing a third portion of the regenerated catalyst from the regeneration zone directly to the mixing zone. Preferably, the third portion is directed from the regeneration zone to the mixing zone to a conduit, referred to herein as a "temperature control catalyst conduit." This embodiment provides for an increased ability to control the temperature of the mixed catalyst in the mixing zone by providing a relatively hot catalyst stream (the third portion) directly to the mixing zone. The flow rate of the third portion optionally is adjustable with a valve to control the temperature of the mixed catalyst in the mixing zone. That is, the temperature of the mixed catalyst can be increased by increasing the flow of the third portion or decreased by decreasing the flow of the third portion.

IV. Systems for Controlling the Temperature During Catalyst Regenerated

Several embodiments of the present invention are directed to systems for implementing the processes of the present invention. In one embodiment, for example, the invention is to a novel catalyst regeneration system for efficiently regenerating heavily coked catalyst particles. The regeneration system comprises: (a) a regeneration zone; (b) a catalyst cooler (optionally comprising a plurality of external catalyst coolers operating in parallel); (c) a mixing zone; (d) a spent catalyst conduit for communicating spent catalyst from a reactor to the mixing zone; (e) a hot catalyst conduit for communicating hot catalyst from the regeneration zone to the catalyst cooler; (f) a cold catalyst conduit for communicating cold catalyst from the catalyst cooler to the mixing zone; (g) a mixed catalyst conduit for communicating the mixed catalyst from the mixing zone to the regeneration zone; and (h) a regenerated catalyst conduit for communicating regenerated catalyst from the regeneration zone to the reactor. As discussed above, an oxygen-containing regeneration medium preferably is added directly into the regeneration zone.

As discussed above, the mixing zone optionally is adapted to receive a fluidizing medium from a fluidizing medium source to transport catalyst in a fluidized manner from the mixing zone to the regeneration zone. The fluidizing medium optionally comprises an oxygen-containing fluidizing medium. The fluidizing medium and the oxygen-containing regeneration medium optionally comprise the same oxygen-containing component. For example, the fluidizing medium and the oxygen-containing regeneration medium optionally comprise air.

As discussed above, the mixing zone optionally comprises one or more coils for cooling the mixed catalyst contained therein.

Also as discussed above, the mixed catalyst conduit optionally comprises a vertically extending conduit for transporting the mixed catalyst in an upward direction; and one or more radially-extending downwardly-angled trough arms for delivering the mixed catalyst to the regeneration zone. Optionally, the trough arms have one or more outlets that are situated substantially over one or more grids, which grids release the oxygen-containing regeneration medium into the regeneration zone.

Optionally, the system further comprises a temperature control catalyst conduit for communicating regenerated catalyst from the regeneration zone directly to the mixing zone. The temperature control catalyst conduit optionally comprises a valve for controlling the flow of the regenerated catalyst communicated so as to control the temperature of the mixed catalyst in the mixing zone.

FIG. 2 illustrates a flow diagram of a catalyst regeneration system, generally designated 200, according to one embodiment of the present invention. As shown, the regeneration system 200 comprises a catalyst regenerator 238, a catalyst cooler 243, a mixing zone 203 and a reactor 201. At least a portion of the at least partially spent catalyst contained reactor 201 is withdrawn and transported, preferably in a fluidized manner, through spent catalyst conduit 237 from the reactor 201 to mixing zone 203. The flow rate of the spent catalyst that is transported through spent catalyst conduit 237 may be controlled by a flow control device 202. In one embodiment, the spent catalyst contained in spent catalyst conduit 237 is first directed to a stripping unit, not shown, wherein the spent catalyst is stripped of interstitial hydrocarbons prior to being directed to mixing zone 203.

Cold catalyst also is received in mixing zone 203 via cold catalyst conduit 244. Thus, spent catalyst from reactor 201 is mixed with cold catalyst from cold catalyst conduit 244 in mixing zone 203. Ideally, mixing zone 203 is situated directly below the catalyst regenerator 238, as shown. As shown, the mixing zone is formed of a cylindrical member having a conical section 206 in fluid communication with mixed catalyst conduit 207. It is contemplated, however, that the mixing zone may not be separate from the mixed catalyst conduit. Thus, in another embodiment, not shown, spent catalyst is mixed with cold catalyst in mixed catalyst conduit 207, rather than in a separate mixing zone. That is, the mixing zone may be situated entirely within mixed catalyst conduit 207.

As shown, the mixed catalyst in mixing zone 203 is directed in an upward manner through a conical section 206, which facilitates the conveyance of a mixed catalyst in mixing zone 203 into mixed catalyst conduit 207. The mixed catalyst is then transported, in a fluidized manner, in an upward (distal) direction through mixed catalyst conduit 207. That is, the mixed catalyst in mixing zone 203 contacts a fluidizing medium 204 under conditions effective to transport the mixed catalyst in a fluidized manner from the mixing zone 203, through mixed catalyst conduit 207, and to a regeneration zone 217. The regeneration zone 217 illustrated is situated in the lower portion (dense phase) of catalyst regenerator 238.

In the embodiment illustrated in FIG. 2, the mixed catalyst in mixed catalyst conduit 207 is yielded from the mixed catalyst conduit 207 via distributor 211. Preferably the distributor comprises a trough arm distributor, for example a Kellogg®-type distributor, as disclosed in U.S. Pat. Nos. 5,635,140 and 6,503,460, both to Miller, et al. It is contemplated, however, that other distributors may be used in addition to, or in place of, a Kellogg®-type distributor. Specifically, the distributor preferably is selected from the group consisting of: a trough arm distributor, a plate distributor, and a cap distributor.

Preferably, distributor 211 is situated at or below the surface 213 of the dense phase that defines the upper-most surface of regeneration zone 217. In the embodiment illustrated, distributor 211 distributes the mixed catalyst in an even manner within the regeneration zone 217. Specifically, the mixed catalyst is yielded from the distributor 211 into a region of the regeneration zone 217 that is directly above regeneration medium introduction grids 212.

In operation, the catalyst regenerator 238 functions in the following manner. An oxygen containing regeneration medium 239 is introduced into catalyst regenerator 238 through one or more grids 212 (two are shown). In the regeneration zone 217, the mixed catalyst, which includes spent catalyst, contacts the oxygen containing regeneration medium 239 under conditions effective to at least partially regenerate the spent catalyst and form regenerated catalyst. The distributor 211 illustrated in FIG. 2 comprises a plurality of trough arms, which are particularly desirable because they provide the ability to yield the mixed catalyst from mixed catalyst conduit 207 into regions within regeneration zone 217 that are situated directly above grids 212, thereby facilitating the contacting of the mixed catalyst with the regeneration medium.

As indicated above, the process of regenerating spent catalyst to form regenerated catalyst is an exothermic process. As a result, unless controlled in some manner, the temperature of the catalyst contained in regeneration zone 217 will increase—potentially exceeding the metallurgical constraints of the metals used to form catalyst regenerator 238. In the embodiment illustrated in FIG. 2, a first portion of a catalyst particles contained in regeneration zone 217 is withdrawn therefrom via hot catalyst conduit 242 and directed, preferably in a fluidized manner, to a catalyst cooler 243. Preferably, the catalyst that is withdrawn from the regeneration zone 217 comprises an aliquot portion of the catalyst particles contained in the regeneration zone 217. The flow rate of the catalyst particles contained in hot catalyst conduit 242 may be controlled by flow control device 214.

The hot catalyst particles that are introduced into catalyst cooler 243 via hot catalyst conduit 242 preferably contact a cooling medium 209, in an indirect manner, under conditions effective to cool the hot catalyst particles and form cold catalyst particles and a heated cooling medium 210. Preferably, the cooling medium 209 comprises water and the heated cooling medium 210 comprises steam. As used herein, the terms "hot," and "cold" are not intended to connote any particular temperatures, but instead are used relative to one another. That is, a hot catalyst has a temperature greater than a cold catalyst.

Ultimately, the cold catalyst formed in catalyst cooler 243 is yielded therefrom via cold catalyst conduit 244. The flow rate of the cold catalyst that is transported through cold catalyst conduit 244 may be controlled by a flow control device 205. As shown, the cold catalyst from catalyst cooler 243 is directed through cold catalyst conduit 244 into mixing zone 203.

A second portion of the catalyst particles contained in regeneration zone 217 preferably is yielded therefrom via regenerated catalyst conduit 241 and transported, preferably in a fluidized manner, therethrough back to reactor 201. Optionally, the flow rate of the regenerated catalyst that is transported through regenerated catalyst conduit 241 may be controlled by flow control device 208. The composition of the catalyst particles transported through hot catalyst conduit 242 and regenerated catalyst conduit 241 may be substantially similar, e.g., aliquot portions of catalyst particles contained in the regeneration zone 217.

The regeneration process also forms gaseous byproducts such as carbon monoxide and/or carbon dioxide, which are yielded from regeneration zone 217 and separated from any entrained catalyst particles in separation devices 218. The resulting separated gaseous byproducts of the regeneration process are then directed to a plenum 219 and ultimately yielded from the catalyst regenerator 238 as flue gas 240. In the embodiment illustrated in FIG. 2, the separation devices 218 comprise cyclone separators, and the separated catalyst particles are returned to the regeneration zone 217 via one or more dip legs.

In one embodiment, a third portion of the catalyst particles in regeneration zone 217 is directed from the regeneration zone 217 directly to the mixing zone 213. Specifically, in this embodiment, a third portion of the catalyst particles contained in regeneration zone 217 is directed through temperature control catalyst conduit 215 from the regeneration zone 217 directly to the mixing zone 203. The flow rate of the catalyst through the temperature control catalyst conduit 215 may be controlled by a flow control device 216. The temperature control catalyst conduit 215 provides for the ability to introduce hot catalyst particles directly into the mixing zone 203, as desired, to maintain optimum temperature conditions in the mixing zone 203 as well as in regeneration zone 217.

V. EXAMPLE

The following prophetic example illustrates that mixing cooled catalyst with spent catalyst in a mixing zone and sending the resulting mixed catalyst to a catalyst regenerator can provide an ideal means for controlling the heat liberated during catalyst regeneration as the amount of coke-on-catalyst increases. In the example, the circulation rate of the cold catalyst relative to the rate of spent catalyst that is directed to a mixing zone was determined at increasing coke levels (up to 4 weight percent coke) in Cases A-D, while maintaining a constant regeneration bed temperature of 1300° F. (704° C.). The spent catalyst temperature was maintained at 1000° F. (538° C.) for each of cases A-E. Cases C and D shows the impact of operating with a high coke content (4%) and a higher cold catalyst temperature on the required recycle rate. The final column in Table 1 (Case E: High Coke Case without Cold Recycle) shows that the system would be exposed to a much higher temperature, e.g., as high as 2300° F. (1260° C.) in this example, in the absence of the cold catalyst recycle.

TABLE 1

Maintaining Regeneration Temperature at High Coke Levels

| | Case A | Case B | Case C | Case D | Case E |
| --- | --- | --- | --- | --- | --- |
| Regeneration Bed Temperature ° F. (° C.) | 1300 (704) | 1300 (704) | 1300 (704) | 1300 (704) | 2300 (1260) |
| Spent Catalyst Temperature ° F. (° C.) | 1000 (538) | 1000 (538) | 1000 (538) | 1000 (538) | 1000 (538) |
| Amount of Coke on Spent Catalyst (wt %) | 1 | 2 | 4 | 4 | 4 |
| Cold Catalyst Circulation Rate; Cold:Spent Catalyst (wt/wt) | 0 | 1 | 3 | 4.5 | 0 |
| Cold Catalyst Temperature ° F. (° C.) | N/A | 1000 (538) | 1000 (538) | 1100 (593) | N/A |

As shown in Table 1, the temperature of the regeneration bed advantageously can be maintained at about 1300° F. (704° C.), even as the amount of coke on the spent catalyst increases, by increasing the ratio of the cooled catalyst to spent catalyst that is directed to the mixing zone according to the present invention. Without a mixing zone, it would be expected that at high coke levels, e.g., at or above 4 wt. % coke, localized hot spots would form within the catalyst regenerator. These hot spots could reach temperatures as high as 2300° F. (1260° C.). Such temperatures would cause significant damage to the catalyst regenerator and to the catalyst particles. By mixing the cooled catalyst with the spent catalyst prior to regeneration, however, the formation of hot spots can be advantageously minimized and temperatures in the catalyst regenerator can be uniformly maintained at or below 1300° F. (704° C.), even at high coke levels.

Having now fully described the invention, it will be appreciated by those skilled in the art that the invention may be performed within a wide range of parameters within what is claimed, without departing from the spirit and scope of the present invention.

We claim:

1. A process for regenerating catalyst, wherein the process comprises the steps of:

(a) mixing spent catalyst from a reactor with cold catalyst from a catalyst cooler in a mixing zone to form a mixed catalyst;

(b) contacting the mixed catalyst with a fluidizing medium under conditions effective to transport the mixed catalyst in a fluidized manner from the mixing zone to a regeneration zone;

(c) contacting the mixed catalyst in the regeneration zone with an oxygen-containing regeneration medium under conditions effective to at least partially regenerate the mixed catalyst and form regenerated catalyst;

(d) directing a first portion of the regenerated catalyst to the catalyst cooler, in which the first portion is cooled to form the cold catalyst mixed in step (a); and (e) directing a second portion of the regenerated catalyst to the reactor.

2. The process of claim 1, wherein the oxygen-containing regeneration medium is added directly into the regeneration zone.

3. The process of claim 1, wherein the fluidizing medium comprises an oxygen-containing fluidizing medium.

4. The process of claim 1, wherein the fluidizing medium and the oxygen-containing regeneration medium comprise the same oxygen-containing component.

5. The process of claim 1, wherein the fluidizing medium and the oxygen-containing regeneration medium comprise air.

6. The process of claim 1, wherein the process further comprises the step of:

(f) cooling the mixed catalyst in the mixing zone with a cooling medium, which cooling medium indirectly contacts the mixed catalyst in the mixing zone through one or more cooling coils.

7. The process of claim 1, wherein the catalyst cooler comprises a plurality of external catalyst coolers operating in parallel.

8. The process of claim 1, wherein the ratio of the feed rate of regeneration medium fed to the regeneration zone to the feed rate of the fluidizing medium fed to the mixing zone is greater than about 5.

9. The process of claim 8, wherein the ratio of the feed rate of regeneration medium fed to the regeneration zone to the feed rate of the fluidizing medium fed to the mixing zone is greater than about 50.

10. The process of claim 9, wherein the ratio of the feed rate of regeneration medium fed to the regeneration zone to the feed rate of the fluidizing medium fed to the mixing zone is greater than about 98.

11. The process of claim 1, wherein the transporting in step (b) comprises the sub-steps of:

(i) directing the mixed catalyst in a fluidized manner upwardly through a vertically extending conduit; and (ii) distributing the mixed catalyst into the regeneration zone through one or more radially-extending downwardly-angled trough arms, a cap or a plate.

12. The process of claim 11, wherein the mixed catalyst is released into the regeneration zone substantially over one or more grids, which grids release the oxygen-containing regeneration medium into the regeneration zone.

13. The process of claim 1, wherein the spent catalyst comprises more than 0.5 weight percent coke, based on the total weight of the spent catalyst and coke thereon.

14. The process of claim 13, wherein the spent catalyst comprises more than 2 weight percent coke, based on the total weight of the spent catalyst and coke thereon.

15. The process of claim 14, wherein the spent catalyst comprises more than 4 weight percent coke, based on the total weight of the spent catalyst and coke thereon.

16. The process of claim 1, wherein the mixed catalyst in the mixing zone has a temperature of from about 427° C. to about 700° C.

17. The process of claim 16, wherein the mixed catalyst in the mixing zone has a temperature of from about 527° C. to about 600° C.

18. The process of claim 1, wherein the mixed catalyst and the regenerated catalyst in the regeneration zone has a temperature of from about 527° C. to about 760° C.

19. The process of claim 18, wherein the mixed catalyst and the regenerated catalyst in the regeneration zone has a temperature of from about 600° C. to about 732° C.

20. The process of claim 1, wherein the ratio of the flow rate of the first portion to the flow rate of the second portion is at least about 1.0.

21. The process of claim 20, wherein the ratio of the flow rate of the first portion to the flow rate of the second portion is at least about 2.0.

22. The process of claim 21, wherein the ratio of the flow rate of the first portion to the flow rate of the second portion is at least about 4.0.

23. The process of claim 1, wherein the process further comprises the step of:

(f) directing a third portion of the regenerated catalyst from the regeneration zone directly to the mixing zone.

24. The process of claim 23, wherein the flow rate of the third portion is adjustable with a valve to control the temperature of the mixed catalyst in the mixing zone.

25. A process for regenerating catalyst, wherein the process comprises the steps of:

(a) mixing spent catalyst from a reactor with cold catalyst from a catalyst cooler in a mixing zone to form a mixed catalyst;

(b) directing a fluidizing medium into the mixing zone at a first feed rate under conditions effective to transport the mixed catalyst in a fluidized manner from the mixing zone to a regeneration zone;

(c) directing an oxygen-containing regeneration medium into the regeneration zone at a second feed rate, wherein the second feed rate is greater than the first feed rate;

(d) contacting the mixed catalyst in the regeneration zone with the oxygen-containing regeneration medium under conditions effective to at least partially regenerate the mixed catalyst and form regenerated catalyst;

(e) directing a first portion of the regenerated catalyst to the catalyst cooler, in which the first portion is cooled to form the cold catalyst mixed in step (a); and (f) directing a second portion of the regenerated catalyst to the reactor.

26. The process of claim 25, wherein the oxygen-containing regeneration medium is added directly into the regeneration zone.

27. The process of claim 25, wherein the fluidizing medium comprises an oxygen-containing fluidizing medium.

28. The process of claim 25, wherein the fluidizing medium and the oxygen-containing regeneration medium comprise the same oxygen-containing component.

29. The process of claim 25, wherein the fluidizing medium and the oxygen-containing regeneration medium comprise air.

30. The process of claim 25, wherein the process further comprises the step of:

(g) cooling the mixed catalyst in the mixing zone with a cooling medium, which cooling medium indirectly contacts the mixed catalyst in the mixing zone through one or more cooling coils.

31. The process of claim 25, wherein the catalyst cooler comprises a plurality of external catalyst coolers operating in parallel.

32. The process of claim 25, wherein the ratio of the second feed rate to the first feed rate is greater than about 5.

33. The process of claim 32, wherein the ratio of the second feed rate to the first feed rate is greater than about 50.

34. The process of claim 33, wherein the ratio of the second feed rate to the first feed rate is greater than about 98.

35. The process of claim 25, wherein the transporting in step (b) comprises the sub-steps of:
  (i) directing the mixed catalyst in a fluidized manner upwardly through a vertically extending conduit; and
  (ii) distributing the mixed catalyst into the regeneration zone through one or more radially-extending downwardly-angled trough arms, a cap or a plate.

36. The process of claim 35, wherein the mixed catalyst is released into the regeneration zone substantially over one or more grids, which grids release the oxygen-containing regeneration medium into the regeneration zone.

37. The process of claim 25, wherein the spent catalyst comprises more than 0.5 weight percent coke, based on the total weight of the spent catalyst and coke thereon.

38. The process of claim 37, wherein the spent catalyst comprises more than 2 weight percent coke, based on the total weight of the spent catalyst and coke thereon.

39. The process of claim 38, wherein the spent catalyst comprises more than 4 weight percent coke, based on the total weight of the spent catalyst and coke thereon.

40. The process of claim 25, wherein the mixed catalyst in the mixing zone has a temperature of from about 427° C. to about 700° C.

41. The process of claim 40, wherein the mixed catalyst in the mixing zone has a temperature of from about 527° C. to about 600° C.

42. The process of claim 25, wherein the mixed catalyst and the regenerated catalyst in the regeneration zone has a temperature of from about 527° C. to about 760° C.

43. The process of claim 42, wherein the mixed catalyst and the regenerated catalyst in the regeneration zone has a temperature of from about 600° C. to about 732° C.

44. The process of claim 25, wherein the ratio of the flow rate of the first portion to the flow rate of the second portion is at least about 1.0.

45. The process of claim 44, wherein the ratio of the flow rate of the first portion to the flow rate of the second portion is at least about 2.0.

46. The process of claim 45, wherein the ratio of the flow rate of the first portion to the flow rate of the second portion is at least about 4.0.

47. The process of claim 25, wherein the process further comprises the step of:
  (g) directing a third portion of the regenerated catalyst from the regeneration zone directly to the mixing zone.

48. The process of claim 47, wherein the flow rate of the third portion is adjustable with a valve to control the temperature of the mixed catalyst in the mixing zone.

* * * * *